(12) United States Patent
Underwood

(10) Patent No.: US 12,171,983 B2
(45) Date of Patent: Dec. 24, 2024

(54) SLIDING FLOW CONTROLLER

(71) Applicant: CareFusion 303, Inc., San Diego, CA (US)

(72) Inventor: Wesley Underwood, Placentia, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/380,942

(22) Filed: Oct. 17, 2023

(65) Prior Publication Data
US 2024/0042129 A1 Feb. 8, 2024

Related U.S. Application Data

(63) Continuation of application No. 17/037,456, filed on Sep. 29, 2020, now Pat. No. 11,819,661.

(51) Int. Cl.
*A61M 5/168* (2006.01)
*A61M 39/28* (2006.01)

(52) U.S. Cl.
CPC .... *A61M 5/16813* (2013.01); *A61M 5/16818* (2013.01); *A61M 5/16881* (2013.01); *A61M 39/287* (2013.01); *A61M 2205/3334* (2013.01); *A61M 2205/583* (2013.01)

(58) Field of Classification Search
CPC .......... A61M 5/16813; A61M 5/16881; A61M 39/28; A61M 39/284; A61M 39/285; A61M 39/286; A61M 39/287; A61M 60/853; F16K 7/06; F16K 7/063; F16K 7/065; F16K 7/066
See application file for complete search history.

(56) References Cited

U.S. PATENT DOCUMENTS

| | | |
|---|---|---|
| 2,092,401 A | 9/1937 | Miller |
| 3,497,175 A | 2/1970 | Koland |
| 3,544,060 A | 12/1970 | Demler |
| 3,625,472 A | 12/1971 | Rychlik |
| 3,630,481 A | 12/1971 | McGay |

(Continued)

FOREIGN PATENT DOCUMENTS

FR 2646085 A1 10/1990

OTHER PUBLICATIONS

International Search Report and Written Opinion for Application No. PCT/US2021/052461, dated Jan. 26, 2022, 15 pages.

*Primary Examiner* — Kami A Bosworth
(74) *Attorney, Agent, or Firm* — Morgan, Lewis & Bockius LLP

(57) ABSTRACT

A flow controller having an internal tubing is provided. The flow controller may include an upper housing having a plurality of graduations, a lower housing engaged with and slidably coupled to the lower housing, and a cavity defined between the upper and lower housings for accommodating at least a portion of internal tubing. The flow controller may further include a flexible clamp having an upper section mounted in the upper housing and a lower section slidably disposed in the lower housing. The upper and lower housings may be slidably coupled relative to each other to transition the internal tubing from (i) an open position where a lumen of the internal tubing is uncompressed by the flexible clamp to (ii) a closed position where the lumen of the tubing is at least partially constricted by the flexible clamp.

20 Claims, 11 Drawing Sheets

(56) References Cited

U.S. PATENT DOCUMENTS

| | | | |
|---|---|---|---|
| 4,065,093 A | | 12/1977 | Phillips |
| 4,243,034 A | | 1/1981 | Brandt |
| 4,262,876 A | | 4/1981 | Willatt |
| 5,830,195 A | * | 11/1998 | Peters ................. A61M 39/286 |
| | | | 604/905 |
| 6,341,757 B1 | | 1/2002 | Starchevich |
| 6,422,529 B1 | | 7/2002 | Adelberg |
| 6,749,591 B1 | | 6/2004 | McNally |
| 8,313,081 B2 | | 11/2012 | Adelberg |
| 8,770,542 B2 | | 7/2014 | Loth et al. |
| 11,040,186 B2 | | 6/2021 | Burkholz |
| 2007/0181835 A1 | | 8/2007 | Hanada |
| 2008/0029721 A1 | | 2/2008 | Miyahara |
| 2010/0168682 A1 | | 7/2010 | Braga |
| 2011/0297854 A1 | | 12/2011 | Loth |
| 2014/0100526 A1 | | 4/2014 | Ueda |
| 2016/0339454 A1 | | 11/2016 | Rhea |
| 2019/0290841 A1 | | 9/2019 | Park et al. |

\* cited by examiner

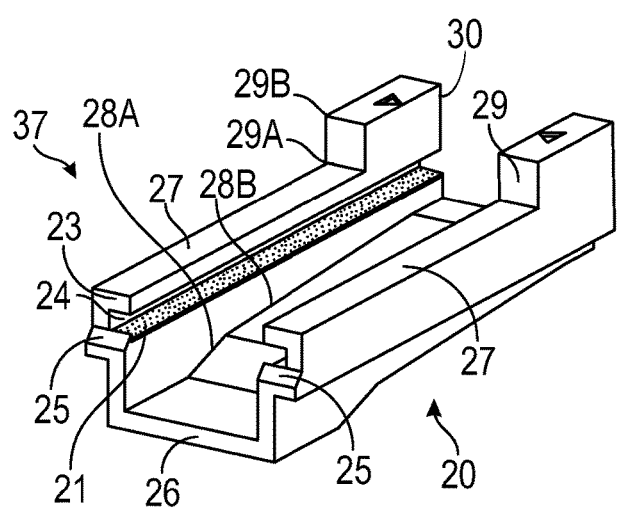
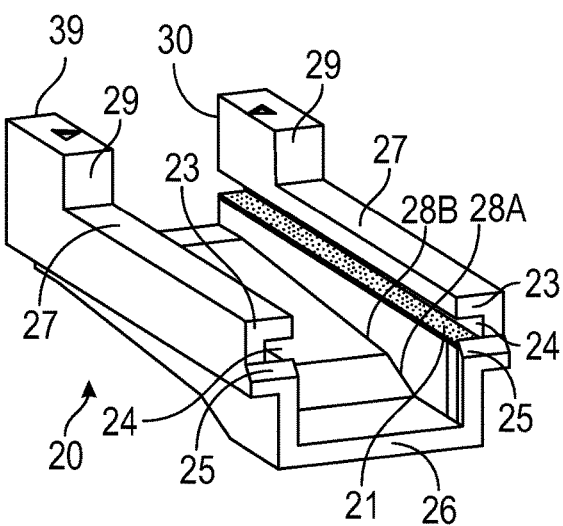
FIG. 11A    FIG. 11B
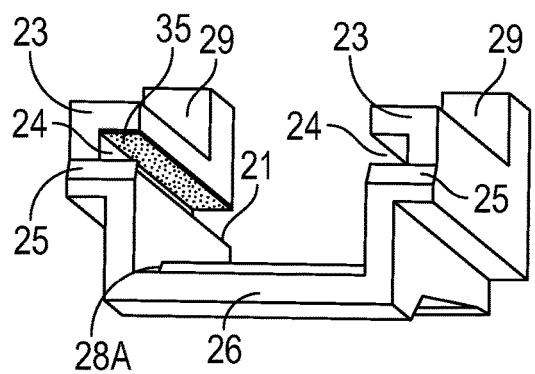
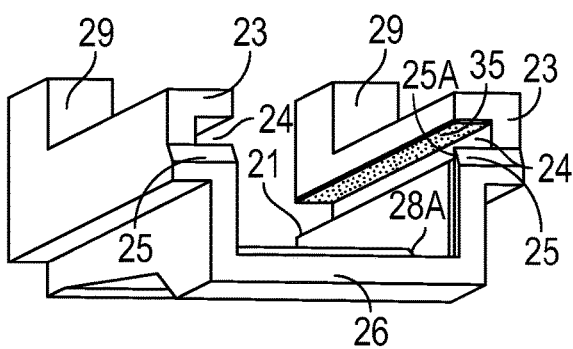
FIG. 12A    FIG. 12B

SLIDING FLOW CONTROLLER

CROSS REFERENCES TO RELATED APPLICATIONS

This application claims the benefit of U.S. patent application Ser. No. 17/037,456 entitled "SLIDING FLOW CONTROLLER," filed on Sep. 29, 2020, issued as U.S. Pat. No. 11,819,661 on Nov. 21, 2023, the disclosure of which is hereby incorporated by reference in its entirety for all purposes.

TECHNICAL FIELD

The present disclosure generally relates to intravenous (IV) fluid administration and, in particular, relates to linearly actuated flow controllers for IV fluid administration.

BACKGROUND

Intravenous (IV) administration sets, sometimes referred to simply as IV sets, for infusion of medical fluids commonly include IV tubing for coupling a medical fluid container such as an IV bag to a patient interface such as a catheter assembly for a patient. In some scenarios, gravity infusion of the medical fluid uses the force of gravity, rather than an infusion pump, to deliver the medical fluid through the IV set. Control of the flow rate through the tubing is often provided by a roller clamp on the IV tubing. However, it can be difficult to provide a desired flow rate using a roller clamp.

SUMMARY

In accordance with various embodiments of the present disclosure, a flow controller having an internal tubing may include an upper housing including a plurality of graduations, a lower housing engaged with and slidably coupled to the lower housing, an internal tubing and a cavity defined between the upper and lower housings for accommodating at least a portion of the internal tubing. The flow controller further includes a flexible clamp having an upper section mounted in the upper housing and a lower section slidably disposed in the lower housing, the upper and lower housings being slidably coupled relative to each other between an open position where a lumen of the internal tubing is uncompressed by the flexible clamp and a closed position where the lumen of the internal tubing is at least partially constricted by the flexible clamp. The lower housing comprises a guide groove extending from a lower proximal face to a lower distal face, wherein a lower protrusion of the upper housing is slidably mounted in the guide groove to move the upper housing relative to the lower housing.

In accordance with various embodiments of the present disclosure, a flow controller for intravenous (IV) tubing may include an upper housing including a plurality of graduations and a lower housing comprising a ramped surface and slidably coupled to the upper housing. The flow controller further includes a flexible clamp mounted in the upper housing and extending into the lower housing, and a flexible internal tubing disposed in a cavity defined between the upper and lower housings, the flexible internal tubing extending through a guide portion of the flexible clamp, wherein the upper housing is configured to slide over the lower housing such that the flexible clamp compresses a portion of the flexible internal tubing. The lower housing comprises a guide groove extending from a lower proximal face to a lower distal face, wherein a lower protrusion of the upper housing is slidably mounted in the guide groove to move the upper housing relative to the lower housing.

Additional advantages of the subject technology will become readily apparent to those skilled in this art from the following detailed description, wherein only certain aspects of the subject technology are shown and described, simply by way of illustration. As will be realized, the subject technology is capable of other and different configurations, and its several details are capable of modifications in various other respects, all without departing from the subject technology. Accordingly, the drawings and description are to be regarded as illustrative in nature, and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIGS. 11A and 11B are perspective views of a lower housing of the sliding flow controller, in accordance with some embodiments of the present disclosure.

FIGS. 12A and 12B are perspective views of a lower housing of the sliding flow controller, in accordance with some embodiments of the present disclosure.

DETAILED DESCRIPTION

Figure 1:
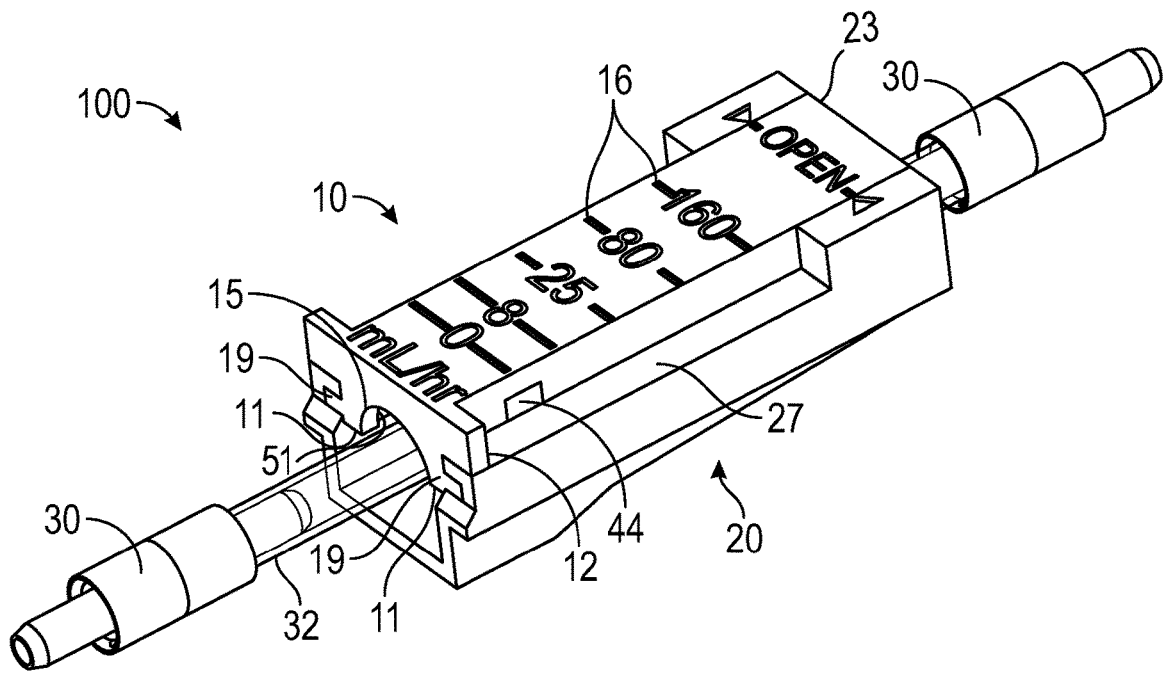
FIG. 1 depicts a perspective view of a sliding flow controller in an open position, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the claims. Various aspects of the subject technology will now be disclosed according to particular but non-limiting examples. Various embodiments described in the present disclosure may be carried out in different ways and variations, and in accordance with a desired application or implementation.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure.

As used herein, the terms "tubing," "fluid line," and any variation thereof refers to medical lines or tubes used to deliver liquids, solvents, or fluids (including gas) to or from a patient under medical care. For example, fluid lines (tubing) may be used for intravenous (IV) delivery of fluids, fluid drainage, oxygen delivery, a combination thereof, and the like.

As used herein, the terms "medical connector," "connector," "fitting," and any variation thereof refer to any device used to provide a fluid flow path between two or more fluid lines coupled thereto.

During administration of infusion therapy via gravity IV set, the clinician will regulate the rate of medication delivered through a flow controller such as a roller clamp or an in-line flow controller. Roller clamps regulate the flow rate of the medication by partially or completely occluding the tubing of the IV set. The IV tubing is occluded by pinching the tubing between a clinician manipulated wheel and angled groove found within the body of the roller clamp. In-line flow controllers regulate the flow rate of the medication as it flows through a tortuous path within the in-line flow controllers. The clinician can adjust the flow rate by rotating the in-line flow controllers, increasing or decreasing the flow rate of the medication as the length of a tortuous path within the in-line flow controllers is increased or decreased.

Various embodiments of the present disclosure are directed to providing a sliding flow controller including an upper housing including a plurality of graduations, a lower housing engaged with and slidably coupled to the lower housing, and a cavity defined between the upper and lower housings for accommodating at least a portion of tubing. The sliding flow controller may include a flexible clamp having an upper section mounted in the upper housing and a lower section slidably disposed in the lower housing. The upper and lower housings may be slidably coupled relative to each other to transition the tubing from (i) an open position where a lumen of the tubing is uncompressed by the flexible clamp to (ii) a closed position where the lumen of the tubing is at least partially constricted by the clamp.

In some aspects, the clinician may adjust the fluid flow rate in an IV tubing that is fluidly coupled to the tubing of the sliding flow controller by actuating the upper housing along the lower housing with a sliding motion. Fully open fluid flow through the tubing occurs at zero actuation, while fully closed flow occurs at maximum actuation (the 0 ml/hr graduation). The clinician may set a given flow rate by actuating the sliding flow controller between fully open and fully closed flow positions.

According to various aspects of the present disclosure, the sliding flow controller may operate to gradually pinch or constrict a lumen of the internal low durometer tubing as the upper housing is slid linearly across the lower housing. To this effect, a portion of the low durometer internal tubing may run through the sliding flow controller. In some embodiments, a luer is bonded to each end of the low durometer internal tubing. The IV tubing may then be coupled to each pf the luers so as to fluidly couple the low durometer internal tubing with the IV tubing so that the fluid may flow through the low durometer tubing within the sliding flow controller.

According to various embodiments of the present disclosure, the internal tubing may be positioned within an aperture of a guide member of the pair of flexible clamp. As the upper housing slides distally relative to the lower housing, the multi-angled ramped surface of the lower housing engages the lower arm of the flexible clamp. The upper arm of the flexible clamp may be held captive (fixed) within the upper housing. During actuation, the engagement of the flexible clamp with the multi-angled ramped surface of the lower housing forces the flexible clamp to close as the lower mounting arm is pivoted or rotated towards the upper arm. This closing actuation causes the aperture between the upper and lower arms to decrease, thereby pinching and constricting a lumen of the internal tubing and decreasing fluid flow therethrough. Accordingly, opening actuation of the sliding flow controller when the upper housing is translated proximally towards a proximal face of the lower housing causes the aperture between the upper and lower arm to increase, thereby increasing fluid flow.

In accordance with some embodiments, the incline angles of the multi-angles ramp surface may be tuned to the internal tubing dimensions so that multiple millimeters of actuation may be needed to adjust the flow rate over the high flow rate range and multiple millimeters of actuation may be required to adjust the flow rate over the low flow rate range. For example, in some embodiments, an incline angle of a first ramp section of the lower housing may be larger than an incline angle of a second ramp section of the lower housing. Accordingly, the sliding flow controller of the various embodiments described herein offers several advantages over the currently existing roller clamp based flow controllers, as detailed below.

In particular, a common issue with current roller clamps is that the fluid flow rate is difficult to adjust at low flow rates (about 45 ml/hr and below). Often, the roller wheel must move several millimeters along the roller clamp body to adjust the flow rate from full open to 150 ml/hr while an adjustment from 45 ml/hr to 25 ml/hr requires a near imperceptible movement of the roller wheel. The sliding flow controller described herein has increased usability (ease of use) across the range of clinically relevant flow rates as compared to current roller clamps. For example, in some embodiments, the sliding flow controller may be designed so that multiple millimeters of actuation are required to regulate fluid flow at high flow rates and multiple millimeters of actuation are also required to regulate fluid flow at low flow rates. Accordingly, the sliding flow controller of the various embodiments described herein improves flow rate adjustability at low and high flow rates by featuring a non-linear ramped surface in the lower housing. The non-linear ramped surface of the lower housing features a series of ramp angles specifically tuned for different ranges of flow rates. Several millimeters of actuation of the upper housing relative to the lower housing may be required to adjust through a range of either low flow rates or high flow rates.

Further, a common issue with current roller clamps is that the roller wheel is often small and knurled, and the small wheel geometry and knurling focuses excessive and/or prolonged pressure on the thumb of the clinician. Clinicians may thus experience thumb fatigue and soreness through their work shift from actuating roller clamps multiple times, especially if the IV tubing has a relatively high durometer. The sliding flow controller described herein has better ergonomic characteristics than current roller clamps, thereby improving clinician comfort. For example, as previously described, the clinician may actuate the sliding flow controller by sliding the upper and lower housings either together to open flow or apart to close flow. The overall dimensions of the sliding flow controller are similar to current flow controllers (e.g., the aforementioned roller clamp-based flow controllers), and it fits easily in the hand. As such, the sliding flow controller can be actuated with one hand and the entire surface of the upper and lower housings can be gripped during actuation, rather than just the top of the wheel surface featured on current roller clamps. Because the sliding flow controller has a larger surface area to grip during actuation than a roller clamp, its ergonomics are better than a current roller clamp.

Furthermore, current roller clamps are often designed so that they are compatible over a range of IV tubing inner and outer diameters. The tubing position is also not tightly constrained within the body of the roller clamp. Combining multiple tubing geometries with variation in where the tubing is positioned within the groove of the roller clamp body results in variation in wheel position along the roller clamp body when setting a given flow rate. Because of variation in wheel position, current roller clamps cannot have any feature or mark indicating flow rate given a wheel position along the roller clamp body. Setting a given flow rate using the sliding flow controller is repeatable by design and there are features (graduations) on the sliding flow controller that indicate flow rate settings.

Additionally, the sliding flow controller of the various embodiments described herein improves repeatability by design because the incline angles of the non-linear ramp surface are tuned for use with a specific diameter low durometer tubing. The sliding flow controller described herein also features a tubing guide member to keep the tubing oriented and held perpendicular to the tubing pinching lower and upper arms of the flexible clamp. Since the low durometer internal tubing geometry may be controlled and the tubing position within the upper and lower arms of the flexible clamp may be controlled, the amount that the tubing is pinched (and therefore fluid flow rate) given an amount of actuation is repeatable. To this effect, the sliding flow controller may feature markings that the clinician can use as an aid to quickly adjust the fluid flow rate as desired.

Figure 2:
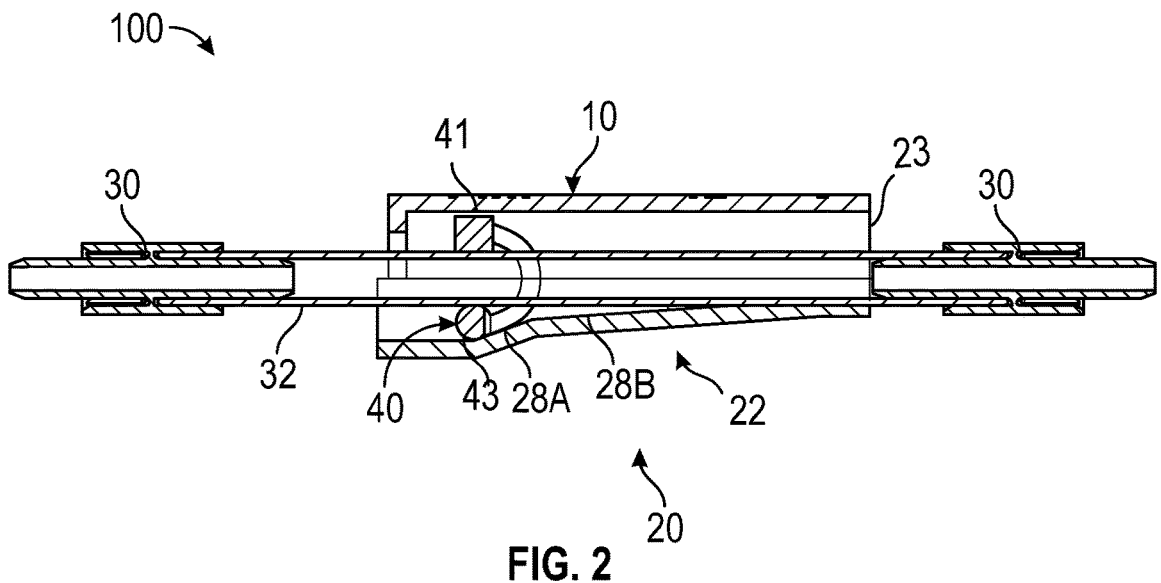
FIG. 2 is a cross-sectional view of the sliding flow controller of FIG. 1, in accordance with some embodiments of the present disclosure.

FIG. 1 depicts a perspective view of a sliding flow controller in an open position, in accordance with some embodiments of the present disclosure. FIG. 2 is a cross-sectional view of the sliding flow controller of FIG. 1, in accordance with some embodiments of the present disclosure. As depicted in FIGS. 1 and 2, a flow controller 100 for intravenous (IV) tubing may include an upper housing 10 including a plurality of graduations 16 and a lower housing 20 engaged with and slidably coupled to the upper housing 10. As depicted, a cavity 15 may be defined between the upper and lower housings 10 and 20 for accommodating at least a portion of a tubing 32. For example, the upper housing 10 may have a first surface 51 that defines a portion of the cavity 15 on a first side of the tubing 32, and the lower housing 20 may have a second surface (i.e., ramped surface 22) that defines a portion of the cavity 15 on a second side of the tubing 32. In some embodiments, the tubing 32 may be fluidly coupled to the IV tubing of an IV set. In these embodiments, a pair of connectors 30 may be disposed at opposing ends of the flexible tubing 32 for connecting the flexible tubing 32 to the IV tubing. For example, the pair of connectors 30 may be luer connectors which fluidly couple the internal flexible tubing 32 of the sliding controller 100 with the IV tubing of the IV set. However, the various embodiments of the present disclosure are not limited to the aforementioned configuration, and the tubing 32 may be the IV tubing.

In some embodiments, as depicted in FIG. 2, the flow controller 100 may further include a flexible clamp 40 having an upper section 41 mounted in the upper housing 10 and a lower section 43 slidably disposed in the lower housing 20. As shall be described in further detail below, the upper and lower housings 10 and 20 may be slidably coupled relative to each other to transition the tubing from (i) an open position (illustrated in FIGS. 1 and 2) where a lumen of the tubing 32 is uncompressed by the clamp 40 to (ii) a closed position (illustrated in FIGS. 3 and 4) where the lumen of the tubing 32 is at least partially constricted by the clamp 40.

Figure 5B:
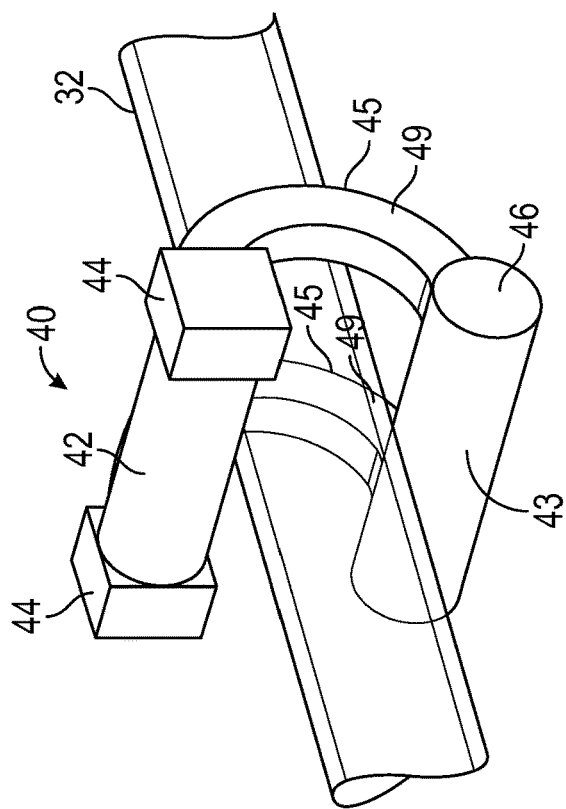
FIG. 5B is a perspective view of the flexible clamp of FIG. 5A having a tubing accommodated therein, in accordance with some embodiments of the present disclosure.
Figure 5C:
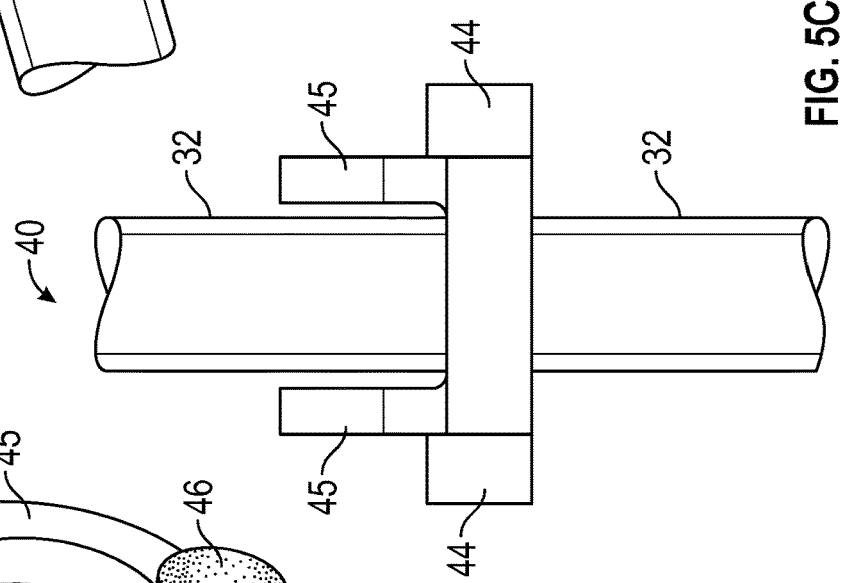
FIG. 5C illustrates a top view of the flexible clamp of FIG. 5A having a tubing accommodated therein, in accordance with some embodiments of the present disclosure.
Figure 5A:
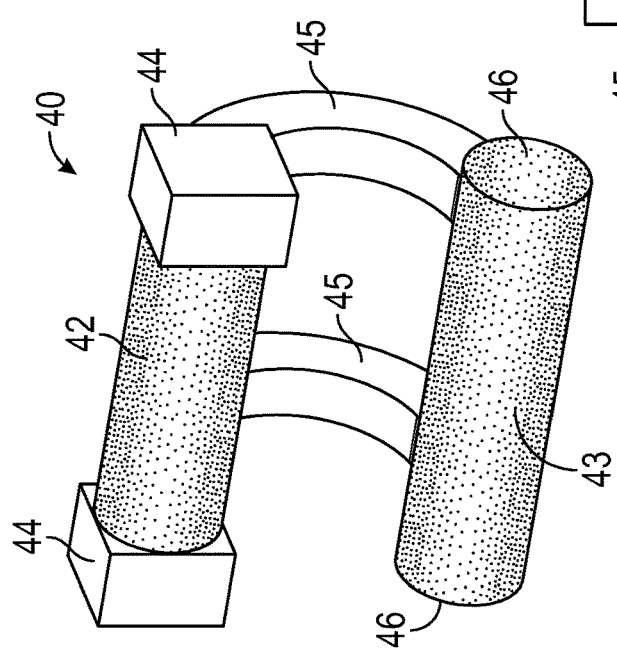
FIG. 5A is a perspective view of a flexible clamp of a sliding flow controller, in accordance with some embodiments of the present disclosure.

FIG. 5A is a perspective view of a flexible clamp of a sliding flow controller, in accordance with some embodiments of the present disclosure. As depicted, the upper section 41 of the flexible clamp 40 may include an upper arm 42 for mounting the flexible clamp 40 in the upper housing 10. In particular, the upper arm 42 may be in the form of a longitudinally extending body including a pair of captive contact members 44 for holding the upper arm 42 captive in the upper housing 10. In particular, the captive contacts 44 may be disposed at opposing ends of the upper arm 42 with the longitudinally extending body coupling the captive contact members 44 to each other. As depicted, the captive contacts 44 may have a square shape. However, the various embodiments of the present disclosure are not limited to the aforementioned configuration. In other embodiments, the captive contacts 44 may have a rectangular or other suitable polygonal shape capable of holding or otherwise restraining the upper arm in the upper housing 10. In particular, since the upper arm is retained or otherwise constrained in the upper housing, motion or translation of the upper housing 10 results in a corresponding to the flexible clamp 40 relative to the lower housing. The lower section 43 of the flexible clamp 40 may include a lower arm 46 in the form of a longitudinally extending body that is disposed in the lower housing 20. As the upper housing 10 is translated or otherwise slid relative to the lower housing 20, the lower arm 46 is also translated and slides against a ramped surface of the lower housing, thereby causing the lower arm 46 to pivot or otherwise rotate towards the upper arm 42 so as to pinch the tubing 32 and constrict the lumen of the tubing to control or otherwise selectively restrict the amount of fluid flowing through the tubing 32. Accordingly, tubing 32 may be a low durometer tubing capable of flexing or otherwise being pinched or compressed by the flexible clamp 40. For example, since the tubing geometry and properties (durometer, inner diameter, outer diameter, concentricity) may be controlled and the body of the sliding flow controller may be tuned to work specifically with the tubing, the expected flow rate given a degree of actuation may be predicted.

FIG. 5B is a perspective view of the flexible clamp of FIG. 5A having an internal tubing 32 accommodated therein, in accordance with some embodiments of the present disclosure. FIG. 5C illustrates a top view of the flexible clamp of FIG. 5A having the internal tubing 32 accommodated therein, in accordance with some embodiments of the present disclosure. Referring to FIGS. 5B and 5C, the flexible clamp 40 may further include a flexible guide member 48 coupling the upper and lower arms 42 and 46 to each other. In particular, as depicted, the flexible guide member 48 may include a pair of hinge arms 49, each extending from the upper arm 43 to the lower arm 46. In some embodiments, each of the hinge arms 49 may be in the form of a curved body having hinge portion 45 about which the lower arm 46 is pivoted or rotated towards the upper arm 42 when the upper housing is translated or slides relative to the lower housing 20. As depicted, the hinge arms 49 may be spaced apart from each other so as to define an aperture 47 through which the tubing 32 may extend. For example, the tubing 32 may extend through the hinge arms 49 of guide member 48 thereby allowing it to be oriented perpendicularly relative to the flexible clamp 40.

Accordingly, when the upper housing 10 is translated or slides relative to the lower housing 20, the lower arm 46 translates and slides against a ramped surface 22 of the lower housing, causing the hinge arms 49 to flex inward and move the lower arm 46 towards the upper arm. Accordingly, the tubing 32 may be pinched or otherwise compressed as the lower arm is pivoted or rotated towards the upper arm 42. As such, a portion of the lumen of the tubing 32 that extends through the aperture 47 may be constricted so as to reduce fluid flow through the tubing 32.

In some embodiments, at least one of the upper arm 42 and the lower arm 46 may have a friction-reducing surface. For example, at least one of the upper arm 42 and the lower arm 46 may be a polished surface, or may be coated or otherwise formed with a friction-reducing material (e.g., grease, oil, a smooth plastic, or the like). Accordingly, when the upper housing is moved relative to the lower housing 20, the lower arm 46 may easily translate and slide against the ramped surface 22 of the lower housing without friction retarding or otherwise opposing the motion.

Figure 6:
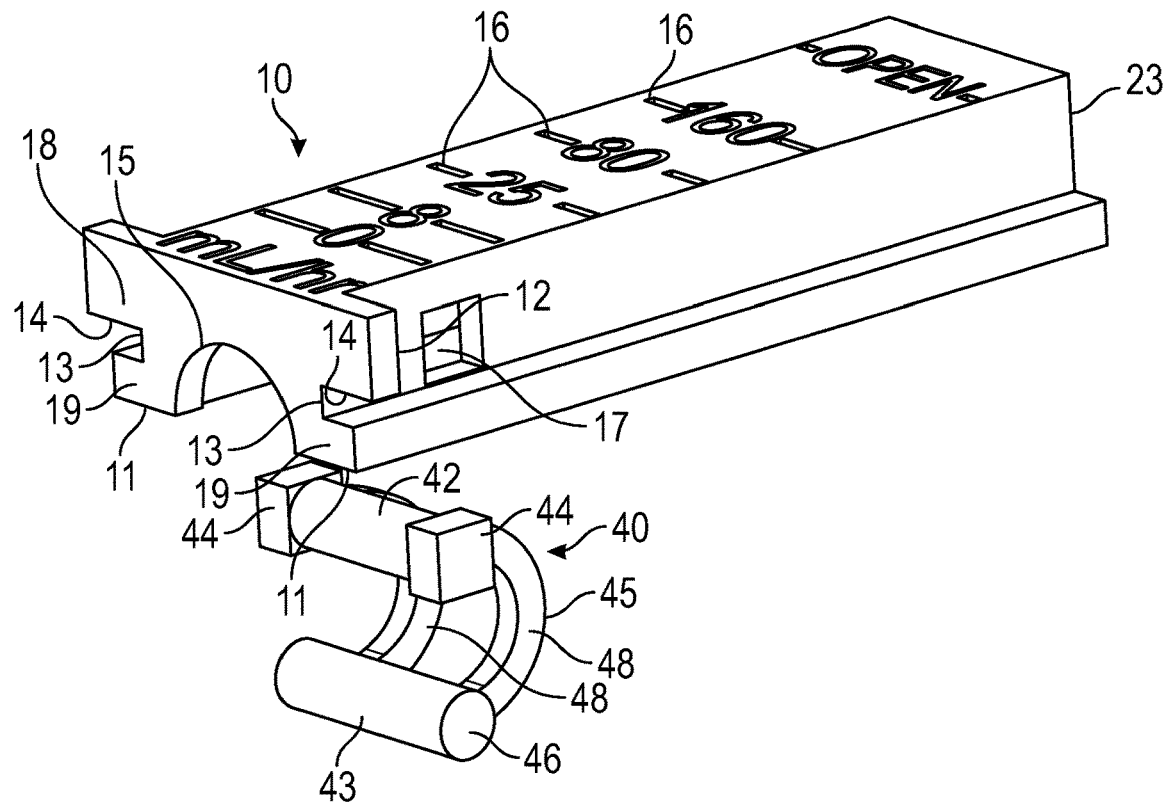
FIG. 6 is a perspective view of an upper housing and flexible clamp of a sliding flow controller, in accordance with some embodiments of the present disclosure.
Figure 7:
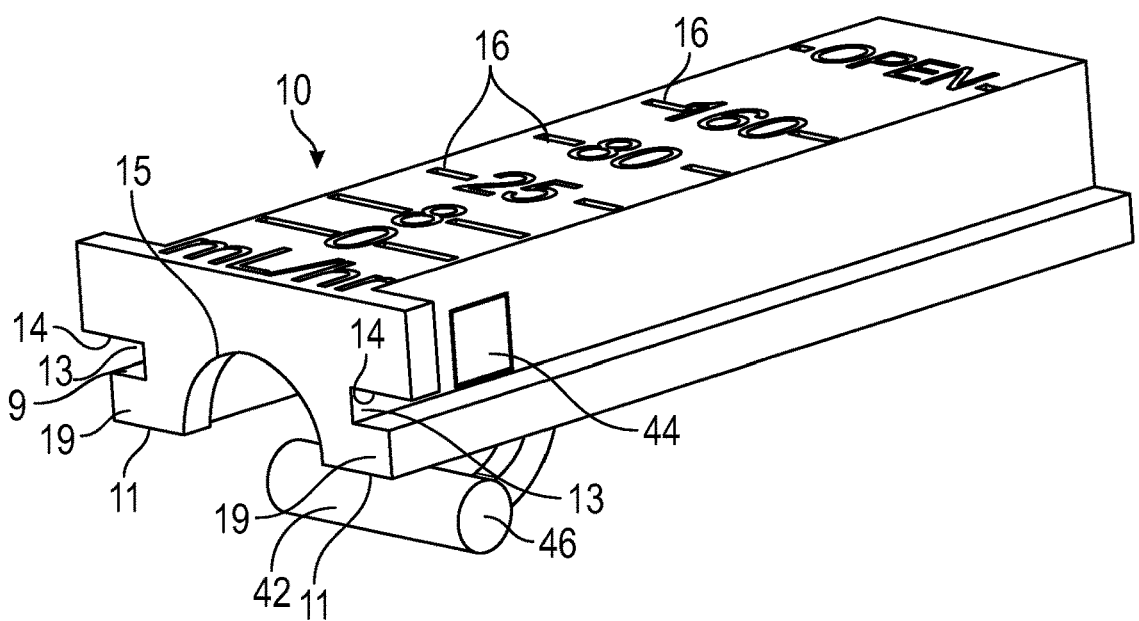
FIG. 7 is a perspective view of the flexible clamp mounted to the upper housing, in accordance with some embodiments of the present disclosure.

FIG. 6 is a perspective view of an upper housing and flexible clamp of a sliding flow controller, in accordance with some embodiments of the present disclosure. FIG. 7 is a perspective view of the flexible clamp mounted to the upper housing, in accordance with some embodiments of the present disclosure.

In accordance with some embodiments, the upper housing 10 may include a pair of mounting apertures 17 positioned axially opposite from each at other a distance corresponding to the opposing ends of the upper arm 42. Accordingly, in the assembled state of the flow controller 100 where the flexible clamp 40 is mounted in the upper housing 10, the captive contacts 44 are mounted in the apertures 17. As such, the upper arm 42 is held captive in the upper housing 10 and prevented from tilting or otherwise rotating about a central longitudinal axis of the cylindrical body of the upper arm 42.

Figure 8:
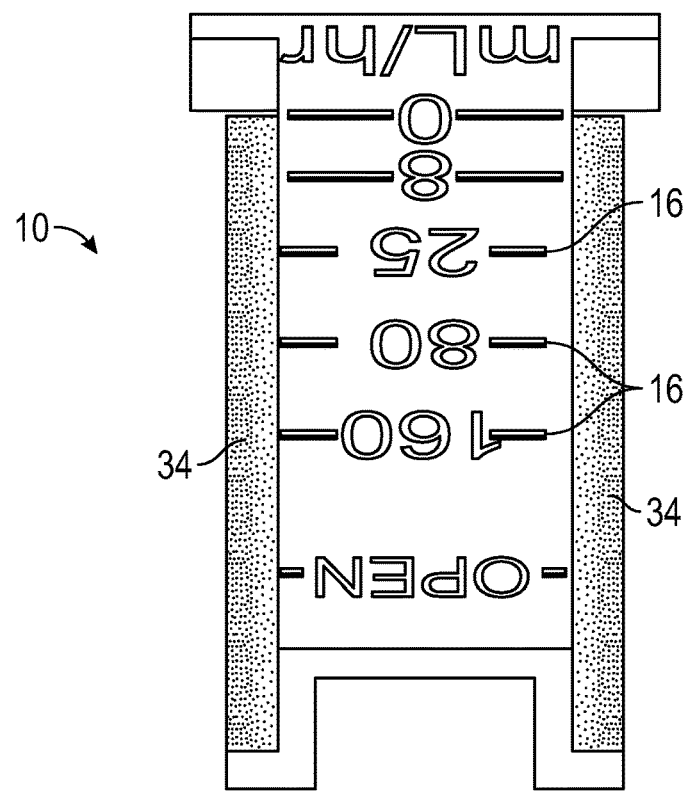
FIG. 8 is a perspective view of a top face of an upper housing of the sliding flow controller, in accordance with some embodiments of the present disclosure.
Figure 9:
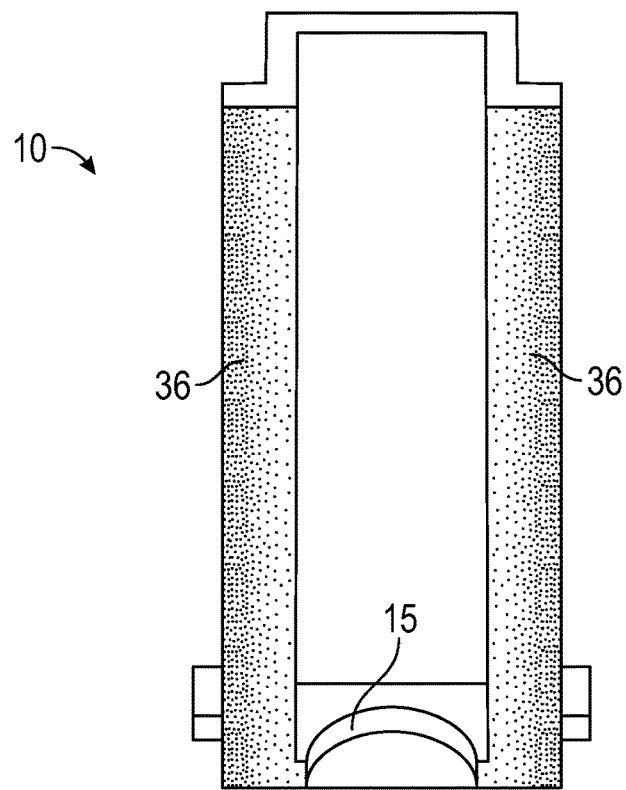
FIG. 9 is a perspective view of a bottom face of an upper housing of the sliding flow controller, in accordance with some embodiments of the present disclosure.

FIG. 8 is a perspective view of a top face of an upper housing of the sliding flow controller, in accordance with some embodiments of the present disclosure. FIG. 9 is a perspective view of a bottom face of an upper housing of the sliding flow controller, in accordance with some embodiments of the present disclosure. Referring to FIGS. 8 and 9, with continued reference to FIGS. 6 and 7, the upper housing 10 may have a proximal face 18 and a distal face 23. Accordingly, the upper housing 10 may extend longitudinally from the proximal face 18 to the distal face 23. As depicted, the proximal face 18 may include an upper protrusion 14, a lower protrusion 19, and a groove 13 defined between the upper and lower protrusions 14 and 19. The lower protrusion 14 may extend longitudinally from the proximal face 18 to the distal face 23. As shall be described in further detail below, the lower protrusion 19 may interface with and be slidably disposed in a corresponding guide groove 24 of the lower housing 20. The lower protrusion 19 may have an upper surface 9 and a lower surface 11. In some embodiments, as illustrated in FIGS. 8 and 9, the upper and lower surfaces 9 and 11 may have respective friction-increasing surfaces. For example, the upper and lower surfaces 9 and 11 may each be textured surfaces such as roughened surfaces 34 and 36 so as to increase friction between the upper and lower surfaces 9 and 11 and the guide groove 24 of the lower housing. The aforementioned configuration is advantageous in preventing unintended actuation (i.e., sliding of the upper housing 10 relative to the lower housing 20) of the sliding flow controller 100.

FIGS. 10A-12B are perspective views of a lower housing of the sliding flow controller, in accordance with some embodiments of the present disclosure. Similar to the upper housing, the lower housing may include a proximal face 26 and a distal face 30. As depicted, the lower housing may extend longitudinally from the proximal face 26 to the distal face 30. A guide groove 24 may be defined along the length of the lower housing 20, extending from the proximal face 26 to the distal face 30. As described above, the lower protrusion 19 may be slidably mounted in the guide groove 24 to allow the upper housing 10 to slide relative to the lower housing 20. In some embodiments, as described above, the lower housing 20 may have a surface 22 that defines a portion of the cavity on a second side of the tubing 32. As depicted, the second surface 22 may be a ramped surface. In operation, as the upper housing 10 is linearly moved or slides over the lower housing 20, the lower arm 46 of the flexible clamp 40 also slides along the ramped surface 22. Because the ramped surface 22 is angled, as the flexible clamp 40 moves or is otherwise slid towards the distal face 30 of the lower housing 20, the lower arm 46 flexes and is pivoted or otherwise deflected upwards a distance corresponding to a vertical component of the gradient or slope of the ramp angle. As the lower arm 46 is deflected upwards towards the upper arm 42, the tubing 32 is pinched and compressed between the upper and lower arms 42 and 46 to reduce or otherwise obstruct stop flow of the medical fluid through the lumen of the tubing 32.

Figure 10A:
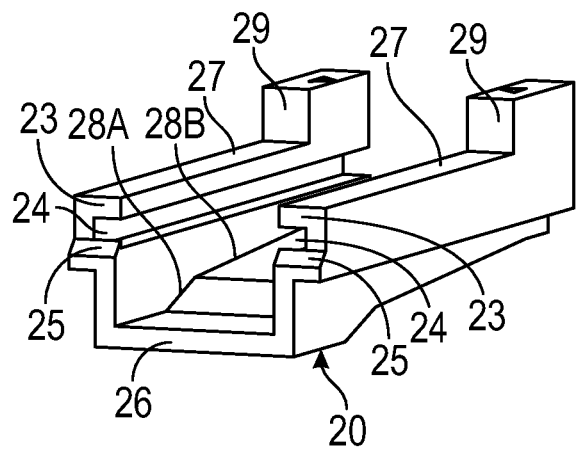
FIGS. 10A and 10B are perspective views of a lower housing of the sliding flow controller, in accordance with some embodiments of the present disclosure.
Figure 10B:
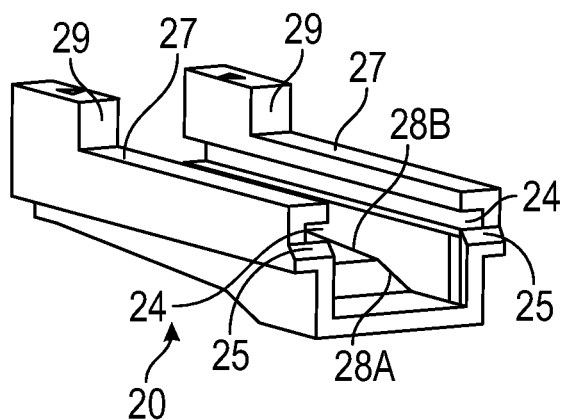

According to various embodiments of the present disclosure, an upper surface 37 of the lower housing 20 may include a first section 27, a second section 39, and a transition step 29 between the first and second sections 27 and 39. The transition step 29 may include a lower end 29A and an upper end 29B. As depicted, the first section 27 may extend from the proximal face 26 of the lower housing 20 to the lower end 29A of the transition step 29, and the second section 39 may extend from the upper end 29B of the transition step 29 to the distal face 30 of the lower housing 20. Accordingly, as illustrated in FIGS. 10A and 10B, the second section 39 may be elevated above the first section 27 at a distance corresponding to a height of the transition step 29. In some embodiments, the transition step 29 may be a stopping surface, such that in a closed state of the sliding flow controller 100 the upper protrusion 14 of the upper housing 10 abuts the stopping surface 29, thereby limiting further distal motion of the upper housing 10 relative to the lower housing 20. In particular, the upper protrusion may include an interface surface 12 that contacts stopping surface 29 when the upper housing 10 reaches the fully closed (0 ml/hr) position.

Figure 3:
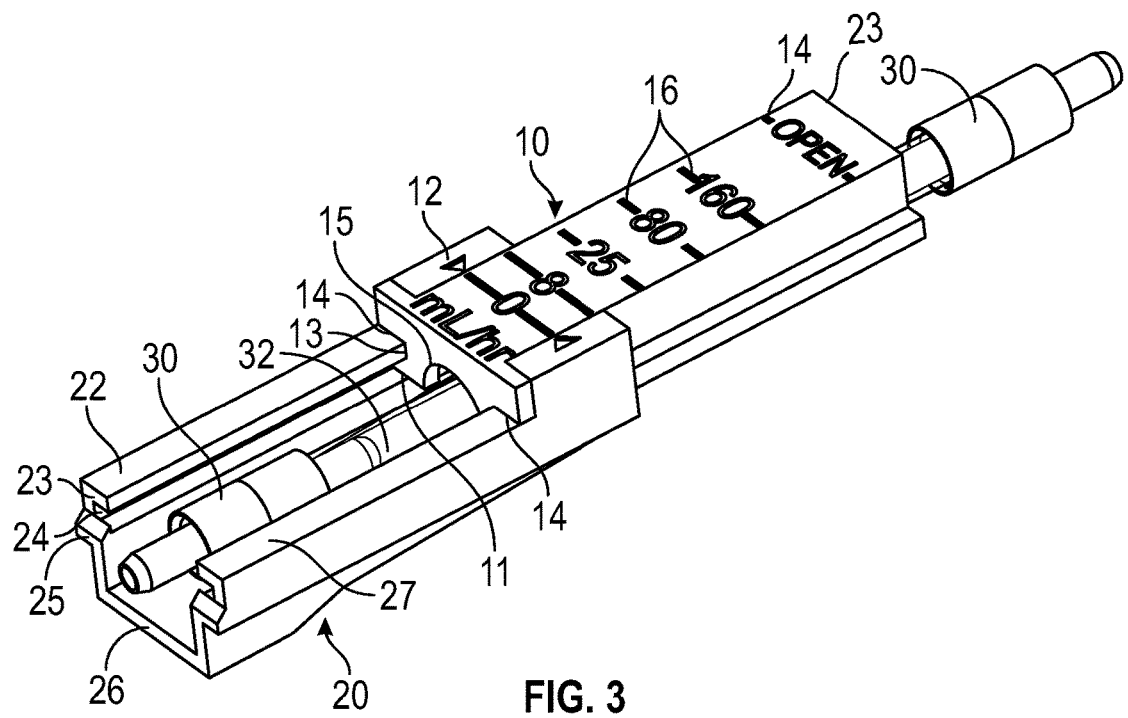
FIG. 3 depicts a perspective view of a sliding flow controller in a closed position, in accordance with some embodiments of the present disclosure.
Figure 4:
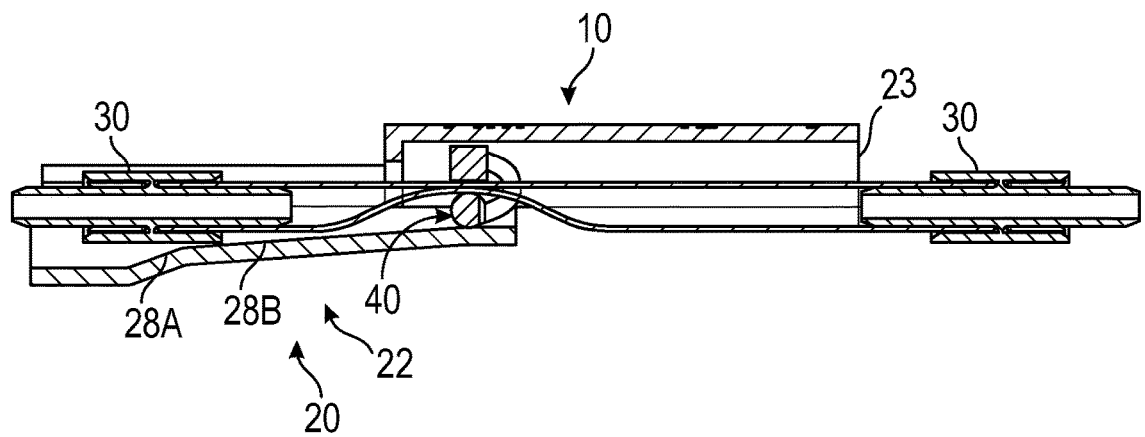
FIG. 4 is a cross-sectional view of the sliding flow controller of FIG. 3, in accordance with some embodiments of the present disclosure.

Stopping surface 29 may be configured to limit the motion of the upper housing 10 relative to the lower housing 20, to provide a tactile indication that upper housing 10 has reached the closed position of FIG. 3, and/or to lock or hold upper housing 10 in the closed position until an opening force or pressure is applied to move the upper housing 10 towards the proximal face 26 of the lower housing 20. Although the stopping surface 29 is shown as being in the form of a transition step 29, the stopping surface 29 may be provided at other locations or using other structural forms. For example, stopping surface 29 may be implemented with complementary structures on upper and lower housings 10 and 20 that interact (e.g., snap together, abut, and/or otherwise interact) to stop motion of the upper housing 10 and to lock the sliding flow controller 100 in the closed configuration.

According to various embodiments of the present disclosure, the proximal face 26 of the lower housing 20 may have a proximal stopping surface 25, which extends across at least a portion of the guide groove 24 at the proximal face 26 of the lower housing 20. In particular, as illustrated, the proximal stopping surface 25 may be in the form of a ramped surface which is angled inwardly (i.e., distally towards the stopping surface 29). Accordingly, as illustrated in FIG. 1, in a fully open state of the sliding flow controller 100 the lower protrusion 19 of the upper housing 10 abuts the stopping surface 25, thereby limiting further proximal motion of the upper housing 10 relative to the lower housing 20. In particular, the proximal stopping surface may include an interface surface 25A that is contacted by the lower protrusion 19 when the upper housing 10 reaches the fully open position.

Accordingly, similar to stopping surface 29, proximal stopping surface 25 may be configured to limit the motion of the upper housing 10 relative to the lower housing 20, to provide a tactile indication that upper housing 10 has reached the fully open position of FIG. 1, and/or to lock or hold upper housing 10 in the open position until an closing force or pressure is applied to move the upper housing 10 distally towards the stopping surface 29 of the lower housing 20. Although the stopping surface 29 is shown as being in the form of a ramped surface the stopping surface 25 may be provided at other locations or using other structural forms. For example, stopping surface 25 may be implemented with complementary structures on upper and lower housings 10 and 20 that interact (e.g., snap together, abut, and/or otherwise interact) to stop motion of the upper housing 10 and to lock the sliding flow controller 100 in the fully open configuration.

In accordance with various embodiments of the present disclosure, the guide groove 24 may include at least one friction-increasing surface. For example, as illustrated in FIGS. 11A and 11B, the guide groove 24 may include a first friction-increasing surface 21. In some embodiments, as illustrated in FIGS. 12A and 12B, the guide groove 24 may include an additional or second friction-increasing surface 35. For example, similar to the textured or roughened surfaces 34 and 36 of upper housing 10, the friction-increasing surfaces 21 and 35 may each be textured or roughened surfaces so as to increase friction between the upper and lower surfaces 9 and 11 and the guide groove 24 of the lower housing. The aforementioned configuration is advantageous in preventing unintended actuation (i.e., sliding of the upper housing 10 relative to the lower housing 20) of the sliding flow controller 100.

Figure 13A:
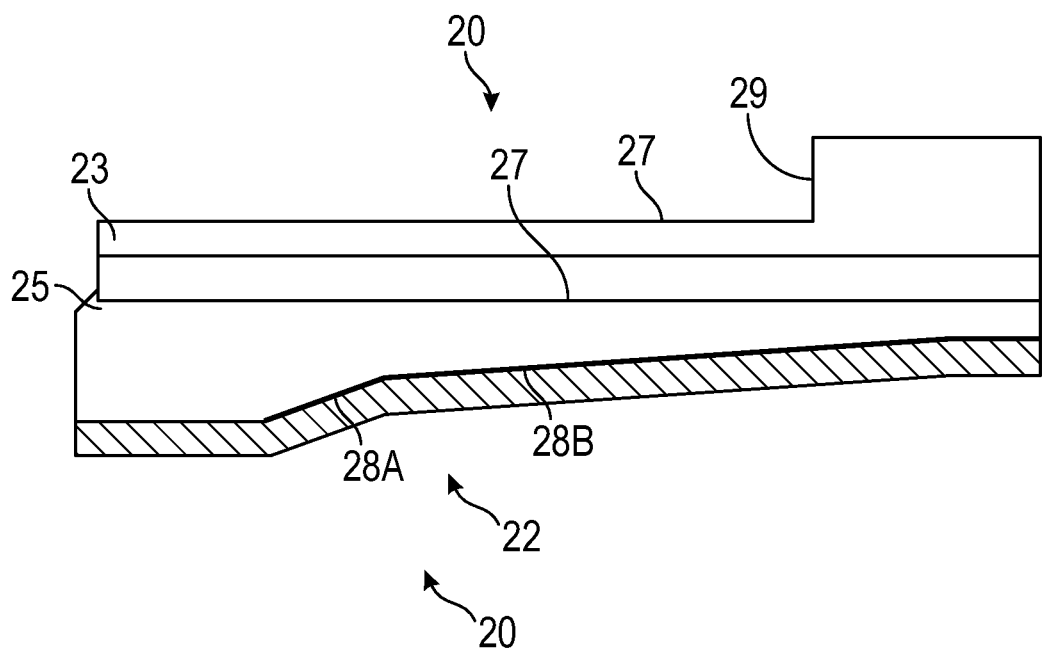
FIG. 13A is a cross-sectional view of a lower housing of the sliding flow controller, in accordance with some embodiments of the present disclosure.

FIG. 13A is a cross-sectional view of the lower housing 20 of the sliding flow controller 100, in accordance with some embodiments of the present disclosure. As depicted, the ramped surface 22 may include a first ramp section 28A having a first incline angle and a second ramp section 28B having a second incline angle different from the first incline angle. In some embodiments, the incline angle of the first ramp section 28A may be larger than the incline angle of the second ramp section 28B. For example, as depicted the gradient or slope of the first ramp section 28A may be steeper or greater than the gradient or slope of the second ramp section 28B. In some embodiments, the incline angle of the first ramp section 28A may be formed steeper or greater than that of the second ramp section 28B in order to control fluid flow through the tubing 32 in the higher fluid flow range of the sliding flow controller 100. For example, the incline angle of the first ramp section 28A may be formed to control flow through the tubing 32 in the region of higher fluid flow rates (e.g., between the fully open and 80 ml/hr flow graduations). Similarly, the incline angle of the second ramp section 28B may be formed flatter or smaller than that of the first section 28 in order to control fluid flow through the tubing 32 in the lower fluid flow range of the sliding flow controller 100. For example, the incline angle of the second ramp section 28B may be formed to control flow through the tubing 32 between the fully closed (0 ml/hr) and 80 ml/hr flow graduations.

As described above, the non-linear ramped surface 22 of the lower housing with multiple ramp sections 28A and 28B having different incline angles may be formed such that the incline angles in the region of high flow rates is higher than the incline angles in the region of low flow rates. Accordingly, given an actuation in the region of high flow rates, the rate of tubing occlusion will occur more quickly than given an actuation in the region of low flow rates. As such, the incline angles of the first and second ramp sections 28A and 28B may be tuned to the tubing geometry so that the actuation needed to set low flow rates uses multiple millimeters of actuation.

Figure 13B:
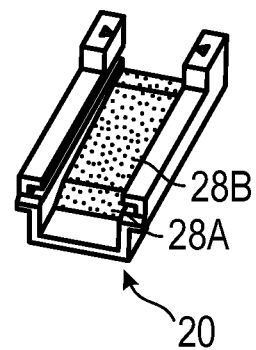
FIG. 13B illustrates a friction-reducing surface of a ramped surface of the lower housing.

FIG. 13B illustrates a friction-reducing surface of a ramped surface 22 of the lower housing 20. In accordance with various embodiments of the present disclosure, the ramped surface 22 may have a friction-reducing surface. For example, ramped surface 22 may be a polished surface, or may be coated or otherwise formed with a friction-reducing material (e.g., grease, oil, a smooth plastic, or the like). Accordingly, when the upper housing is moved relative to the lower housing 20, the lower arm 46 may easily translate and slide against the ramped surface 22 of the lower housing 20 without friction retarding or otherwise opposing the motion.

Figure 14A:
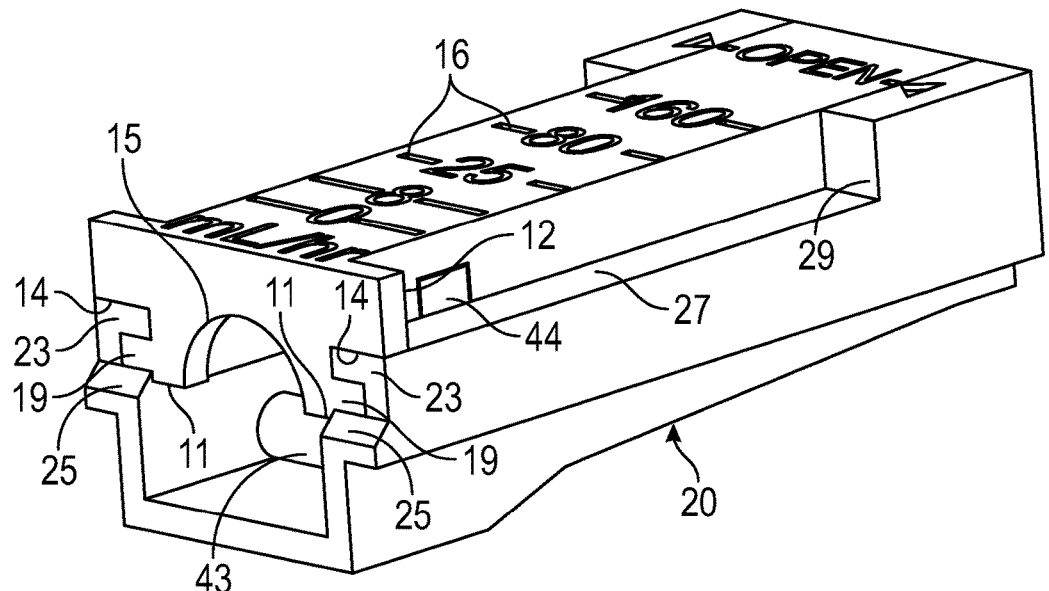
FIG. 14A is a perspective view of an assembly of an upper housing, flexible clamp, and a lower housing of a sliding flow controller in a fully open state, in accordance with some embodiments of the present disclosure.
Figure 14B:
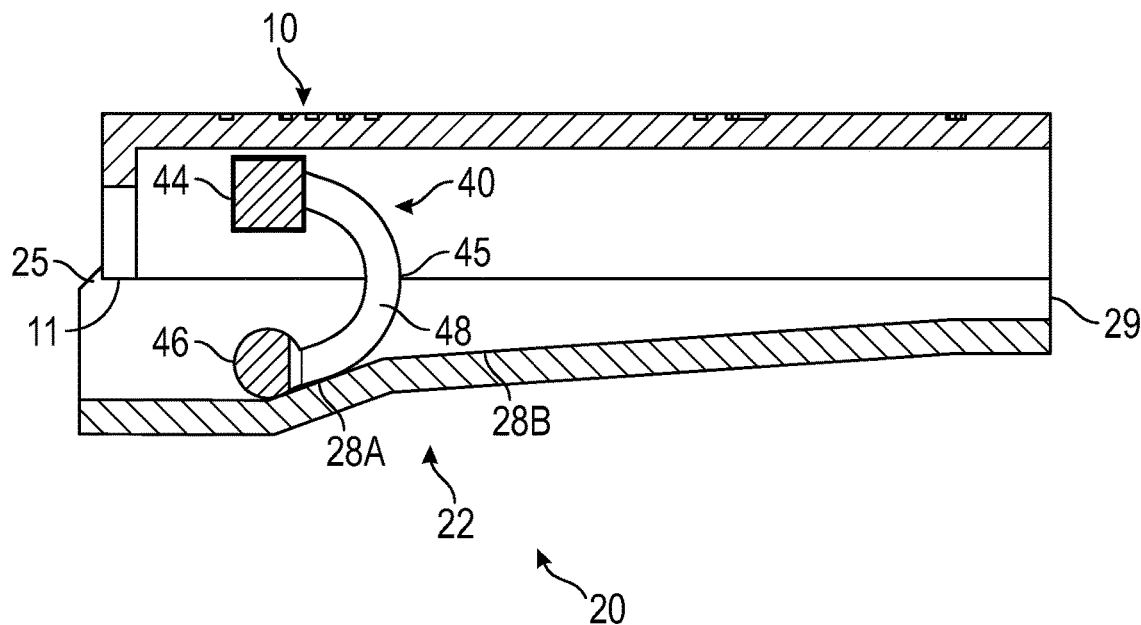
FIG. 14B is a cross-sectional view of the assembly of an upper housing, flexible clamp, and a lower housing of FIG. 14A, in accordance with some embodiments of the present disclosure.

FIGS. 14A-14E illustrate an assembly of an upper housing 10, flexible clamp 40, and a lower housing 20 of a sliding flow controller 100 in a fully open state, in accordance with some embodiments of the present disclosure. FIG. 14A is a perspective view of an assembly of an upper housing, flexible clamp, and a lower housing of a sliding flow controller in a fully open state, in accordance with some embodiments of the present disclosure. FIG. 14B is a cross-sectional view of the assembly of an upper housing, flexible clamp, and a lower housing of FIG. 14A, in accordance with some embodiments of the present disclosure. In the example of FIGS. 14A and 14B, the flow controller 100 is shown in a fully open configuration in which the upper housing 10 is disposed in an open position in which the tubing 32 (not illustrated for ease of viewing the interconnection of components of the assembly) is not compressed. As depicted, in the fully open position, the flexible clamp 40 is positioned with the lower arm 46 on the first ramp section 28A of the lower housing 20. In the fully open position, the flexible clamp 40 may be in an un-flexed or non-compressed state illustrated in FIG. 14B.

In operation, the upper housing 10 may be translated or slid relative to the lower housing 20 in response to a pressure from a user directly on an outer surface of the upper housing 10. Accordingly, the lower arm 46 may translate and slide against the first ramp section 28A towards the second ramp section 28B of the lower housing 20, causing the hinge arms 49 to flex radially inward and move the lower arm 46 towards the upper arm 42. Accordingly, the tubing 32 may be pinched or otherwise compressed as the lower arm 46 is pivoted or rotated towards the upper arm 42. As such, a portion of the lumen of the tubing 32 which extends through the aperture 47 of guide member 48 (illustrated in FIG. 5B) may be constricted so as to reduce fluid flow through the tubing 32.

Figure 14C:
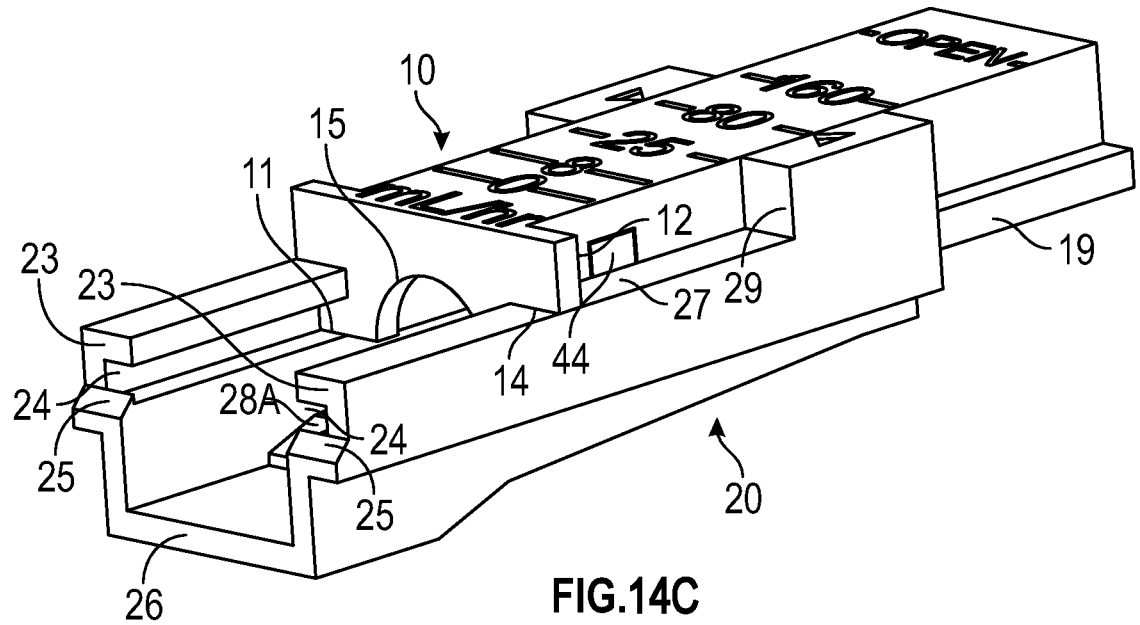
FIG. 14C is a perspective view of an assembly of an upper housing, flexible clamp, and a lower housing of a sliding flow controller, in accordance with some embodiments of the present disclosure.

FIG. 14C shows a perspective view of flow controller 100 after the upper housing has been slid linearly from the fully open position shown in FIGS. 14A and 14B to a partially open position in which a portion of tubing 32 (not illustrated for ease of viewing the interconnection of components of the assembly) may be partially compressed by the flexible clamp 40 between the upper and lower housings 10 and 20. As the upper housing 10 is further translated or otherwise slid relative to the lower housing 20, the lower arm 46 is also translated and slides against second ramp section 28B of the lower housing, thereby causing the lower arm 46 to further pivot or otherwise rotate towards the upper arm 42 so as to further pinch the tubing 32 and further constrict the lumen of the tubing 32 to control or otherwise selectively restrict the amount of fluid flowing through the tubing 32.

Figure 14D:
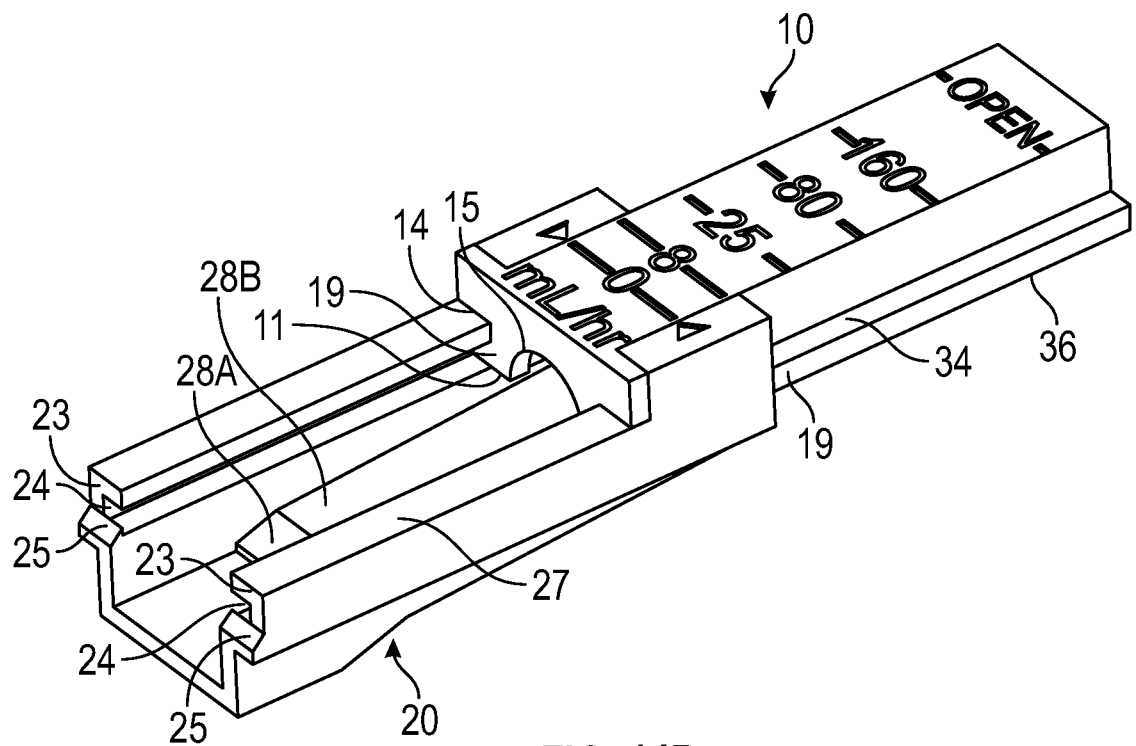
FIG. 14D is a perspective view of an assembly of an upper housing, flexible clamp, and a lower housing of a sliding flow controller in a closed state, in accordance with some embodiments of the present disclosure.
Figure 14E:
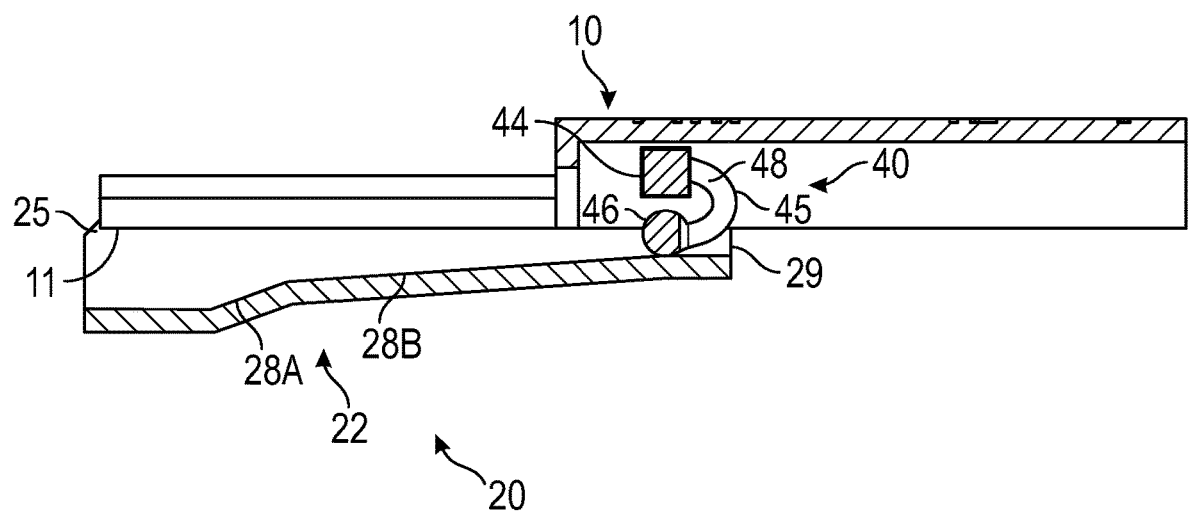
FIG. 14E is a cross-sectional view of the assembly of an upper housing, flexible clamp, and a lower housing of FIG. 14D, in accordance with some embodiments of the present disclosure.

FIG. 14D is a perspective view of an assembly of an upper housing, flexible clamp, and a lower housing of a sliding flow controller in a closed state, in accordance with some embodiments of the present disclosure. FIG. 14E is a cross-sectional view of the assembly of an upper housing, flexible clamp, and a lower housing of FIG. 14D, in accordance with some embodiments of the present disclosure. In operation, as the upper housing 10 is further translated or otherwise slid distally relative to the lower housing 20, the lower arm 46 is also translated and slides further distally against the second ramp section 28B of the lower housing, thereby causing the lower arm 46 to further pivot or otherwise rotate towards the upper arm 42 so as to further pinch the tubing 32 and fully constrict the lumen of the tubing 32 to block fluid from flowing through the tubing 32.

As previously described, stopping surface 29 (illustrated in FIGS. 10A-13A) may limit the motion of the upper housing 10 relative to the lower housing 20, to provide a tactile indication that upper housing 10 has reached the closed position of FIG. 14D. Stopping surface 29 may also lock or hold upper housing 10 in the closed position until an opening force or pressure is applied to move the upper housing 10 proximally towards the proximal face 26 of the lower housing 20.

Accordingly, the upper housing 10 may be slidable relative to the lower housing 20 and can be moved linearly (e.g., slid) between (i) the open position of FIGS. 14A and 14B, at which tubing 32 may be uncompressed within the aperture 47 of guide member 48, and (ii) the closed position, linearly separated from the open position and shown in FIGS. 14D and 14E, in which the tubing 32 is compressed between the upper and lower arms 42 and 46 of the flexible clamp to stop flow of the medical fluid through the tubing 32. As such, the sliding flow controller of the various embodiments described herein advantageously provides improved fluid flow capabilities as compared with currently existing roller clamp-based flow controllers. In particular, as the upper housing 10 is moved distally relative to the lower housing 20, and the lower arm 46 of the flexible clamp 40 is flexed, rotated, or otherwise pivoted towards the upper arm 42, the low durometer internal tubing is gradually occluded, thereby decreasing fluid flow therethrough.

In accordance with various embodiments of the present disclosure, linearly slidable upper housing 10 is continuously slidable between the open position of FIGS. 14A and 14B and the closed position of FIGS. 14D and 14E. Each intermediate position of the linearly slidable upper housing 10 between the open position and the closed position may be associated with an intermediate compression of tubing 32 between the upper and lower arms 42 and 46 of the flexible clamp to set a corresponding intermediate flow rate through the tubing, as illustrated in FIG. 14C.

Accordingly, the sliding flow controller of the various embodiments described herein offers several advantages over the currently existing roller clamp based flow controllers, as detailed below.

In particular, a common issue with current roller clamps is that the fluid flow rate is difficult to adjust at low flow rates (about 45 ml/hr and below). Often, the roller wheel must move several millimeters along the roller clamp body to adjust the flow rate from full open to 150 ml/hr while an adjustment from 45 ml/hr to 25 ml/hr requires a near imperceptible movement of the roller wheel. The sliding flow controller described herein has increased usability (ease of use) across the range of clinically relevant flow rates as compared to current roller clamps. For example, in some embodiments, the sliding flow controller may be designed so that multiple millimeters of actuation are required to regulate fluid flow at high flow rates and multiple millimeters of actuation are also required to regulate fluid flow at low flow rates. Accordingly, the sliding flow controller of the various embodiments described herein improves flow rate adjustability at low and high flow rates by featuring a non-linear ramped surface in the lower housing. The non-linear ramped surface of the lower housing features a series of ramp angles specifically tuned for different ranges of flow rates. Several millimeters of actuation of the upper housing relative to the lower housing may be required to adjust through a range of either low flow rates or high flow rates.

Further, a common issue with current roller clamps is that the roller wheel is often small and knurled, and the small wheel geometry and knurling focuses excessive and/or prolonged pressure on the thumb of the clinician. Clinicians may thus experience thumb fatigue and soreness through their work shift from actuating roller clamps multiple times, especially if the IV tubing has a relatively high durometer. The sliding flow controller described herein has better ergonomic characteristics than current roller clamps, thereby improving clinician comfort. For example, as previously described, the clinician may actuate the sliding flow controller by sliding the upper and lower housings either together to open flow or apart to close flow. The overall dimensions of the sliding flow controller are similar to current flow controllers, e.g., the aforementioned roller clamp-based flow controllers) and it fits easily in the hand. As such, the sliding flow controller can be actuated with one hand and the entire surface of the upper and lower housings can be gripped during actuation, rather than just the top of the wheel surface featured on current roller clamps. Because the sliding flow controller has a larger surface area to grip during actuation than a roller clamp, its ergonomics are better than a current roller clamp.

Furthermore, current roller clamps are often designed so that they are compatible over a range of IV tubing inner and outer diameters. The tubing position is also not tightly constrained within the body of the roller clamp. Combining multiple tubing geometries with variation in where the tubing is positioned within the groove of the roller clamp body results in variation in wheel position along the roller clamp body when setting a given flow rate. Because of variation in wheel position, current roller clamps cannot have any feature or mark indicating flow rate given a wheel position along the roller clamp body. Setting a given flow rate using the sliding flow controller is repeatable by design and there are features (graduations) on the sliding flow controller that indicate flow rate settings.

Additionally, the sliding flow controller of the various embodiments described herein improves repeatability by design because the incline angles of the non-linear ramped surface are tuned for use with a specific diameter low durometer tubing. Because the tubing geometry and properties (durometer, inner diameter, outer diameter, concentricity) may be controlled and the upper and lower housings (i.e., the body) of the sliding flow controller may be tuned to work specifically with the desired tubing, the expected flow rate given a degree of actuation may be more easily predicted.

The sliding flow controller described herein also features a tubing guide member to keep the tubing oriented and held perpendicular to the tubing pinching lower and upper arms of the flexible clamp. Since the low durometer internal tubing geometry may be controlled and the tubing position within the upper and lower arms of the flexible clamp may be controlled, the amount that the tubing is pinched (and therefore fluid flow rate) given an amount of actuation is repeatable. To this effect, the sliding flow controller may feature markings that the clinician can use as an aid to quickly adjust the fluid flow rate as desired.

The subject technology is illustrated, for example, according to various aspects described above. The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. Method claims may be provided to present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary and Brief Description of the Drawings are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in any claim. Rather, as the following claims reflect, inventive subject matter lies in less than all features of a single disclosed configuration or operation.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A flow controller, comprising:
an upper housing including a plurality of graduations;
a lower housing engaged with and slidably coupled to the upper housing linearly and without rotation;
an internal tubing;
a cavity defined between the upper and lower housings for accommodating at least a portion of the internal tubing; and
a flexible clamp having an upper section mounted in the upper housing and a lower section slidably disposed in the lower housing, the upper and lower housings being slidably coupled relative to each other between an open position where a lumen of the internal tubing is uncompressed by the flexible clamp and a closed position where the lumen of the internal tubing is at least partially constricted by the flexible clamp,
wherein the lower housing comprises a first side wall comprising an internal guide groove disposed on an interior surface of the first side wall and facing into the cavity and extending from a lower proximal face to a lower distal face, wherein a lower protrusion of the upper housing is slidably mounted in the internal guide groove within the lower housing to move the upper housing relative to the lower housing.

2. The flow controller of claim 1, wherein the upper section of the flexible clamp comprises an upper arm disposed orthogonally to a longitudinal axis of the upper housing, the upper arm comprising a pair of captive contact members each disposed at opposing ends of the upper arm.

3. The flow controller of claim 2, wherein the lower section comprises a lower arm, and the flexible clamp further comprises a flexible guide member coupling the upper and lower arms to each other.

4. The flow controller of claim 3, wherein:
the upper and lower arms each comprises a cylindrical longitudinally extending body;
the cylindrical longitudinally extending body of the upper arm couples the captive contact members to each other;
the cylindrical longitudinally extending body of the lower arm is slidably mounted in the lower housing; and
the flexible guide member comprises a pair of hinge arms, each of the hinge arms coupling the cylindrical longitudinally extending bodies of the upper and lower arms to each other.

5. The flow controller of claim 4, wherein the hinge arms are spaced apart from each other to define an aperture through which the internal tubing extends.

6. The flow controller of claim 1, wherein the upper housing has a first surface that defines a portion of the cavity on a first side of the internal tubing, the lower housing has a second surface that defines a portion of the cavity on a second side of the internal tubing, and the second surface is a ramped surface.

7. The flow controller of claim 6, wherein the ramped surface comprises a first ramp section having a first incline angle relative to a longitudinal axis of the lower housing and a second ramp section having a second incline angle relative to the longitudinal axis of the lower housing different from the first incline angle.

8. The flow controller of claim 7, wherein the first incline angle is greater than the second incline angle.

9. The flow controller of claim 1, wherein the upper housing comprises an upper proximal face and an upper distal face, the upper housing extending longitudinally from the upper proximal face to the upper distal face, and wherein the upper proximal face comprises an upper protrusion, the lower protrusion, and a groove defined between the upper and lower protrusions, the lower protrusion extending longitudinally from the upper proximal face to the upper distal face.

10. The flow controller of claim 9, wherein the lower housing extends longitudinally from the lower proximal face to the lower distal face.

11. The flow controller of claim 10, wherein an upper surface of the lower housing comprises a first section, a second section, and a transition step between the first and second sections, and wherein:

the transition step comprises a lower end and an upper end, the first section extends from the lower proximal face of the lower housing to the lower end of the transition step; and the second section extends from the upper end of the transition step to the lower distal face of the lower housing.

12. The flow controller of claim 11, wherein the second section is elevated above the first section at a distance corresponding to a height of the transition step, and the transition step comprises a stopping surface, wherein in a closed state of the flow controller, the upper protrusion of the upper housing abuts the stopping surface.

13. The flow controller of claim 10, wherein the lower proximal face of the lower housing comprises a proximal stopping surface extending across at least a portion of the internal guide groove at the lower proximal face of the lower housing, wherein, in an open state of the flow controller, the lower protrusion of the upper housing abuts the proximal stopping surface.

14. The flow controller of claim 1, wherein the internal tubing comprises low durometer tubing, the flow controller further comprising a pair of luer fittings disposed at opposing ends of the internal tubing for coupling the internal tubing to an intravenous (IV) set tubing.

15. A flow controller for intravenous (IV) tubing, the flow controller comprising:
an upper housing including a plurality of graduations;
a lower housing comprising a ramped surface and slidably coupled to the upper housing linearly and without rotation;
a flexible clamp mounted in the upper housing and extending into the lower housing; and
a flexible internal tubing disposed in a cavity defined between the upper and lower housings, the flexible internal tubing extending through a guide portion of the flexible clamp, wherein the upper housing is configured to slide over the lower housing such that the flexible clamp compresses a portion of the flexible internal tubing,
wherein the lower housing comprises a first side wall comprising a guide groove disposed in an interior surface of the first side wall facing into the cavity and extending from a lower proximal face to a lower distal face, wherein a lower protrusion of the upper housing is slidably mounted in the guide groove within the lower housing to move the upper housing relative to the lower housing.

16. The flow controller of claim 15, wherein the ramped surface comprises a first section having a first incline angle relative to a longitudinal axis of the lower housing and a second section having a second incline angle relative to the longitudinal axis of the lower housing and smaller than the first incline angle.

17. The flow controller of claim 15, wherein the upper housing extends longitudinally between an upper proximal face and an upper distal face, and wherein the upper proximal face comprises an upper protrusion, the lower protrusion, and a groove defined between the upper and lower protrusions, the lower protrusion extending longitudinally from the upper proximal face to the upper distal face.

18. The flow controller of claim 15, wherein at least one of the lower protrusion and the guide groove comprises at least one friction-increasing surface.

19. The flow controller of claim 15, wherein the flexible clamp comprises an upper arm mounted in the upper housing and a lower arm extending into the lower housing to engage the ramped surface, the lower arm comprising a friction-reducing surface.

20. The flow controller of claim 19, wherein the lower proximal face of the lower housing comprises a proximal stopping surface extending across at least a portion of the guide groove at the lower proximal face of the lower housing, wherein, in an open state of the flow controller, the lower protrusion of the upper housing abuts the proximal stopping surface.

* * * * *